(12) United States Patent
Lord et al.

(10) Patent No.: US 6,652,510 B2
(45) Date of Patent: Nov. 25, 2003

(54) IMPLANTABLE INFUSION DEVICE AND RESERVOIR FOR SAME

(75) Inventors: Peter C. Lord, Valencia, CA (US); William A. Brandt, Castaic, CA (US); Scott R. Gibson, Granada Hills, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 0 days.

(21) Appl. No.: 10/033,377

(22) Filed: Dec. 26, 2001

(65) Prior Publication Data

US 2003/0050623 A1 Mar. 13, 2003

Related U.S. Application Data

(60) Provisional application No. 60/317,880, filed on Sep. 7, 2001.

(51) Int. Cl.$^7$ .................................................. A61K 9/22
(52) U.S. Cl. .............. 604/892.1; 604/140; 128/DIG. 12
(58) Field of Search .......................... 604/890.1, 891.1, 604/892.1, 140, 141, 153

(56) References Cited

U.S. PATENT DOCUMENTS

| | | | |
|---|---|---|---|
| 4,573,994 A | 3/1986 | Fischell et al. | |
| 4,697,622 A | * 10/1987 | Swift et al. | 141/1 |
| 4,969,873 A | 11/1990 | Steinbach et al. | |
| 5,167,633 A | 12/1992 | Mann et al. | |
| 5,176,644 A | 1/1993 | Srisathapat et al. | |
| 5,514,103 A | 5/1996 | Srisathapat et al. | |
| 5,527,307 A | 6/1996 | Srisathapat et al. | |
| 6,280,416 B1 | * 8/2001 | Van Antwerp et al. | 604/141 |

* cited by examiner

Primary Examiner—Dennis Ruhl
Assistant Examiner—Linh Truong
(74) Attorney, Agent, or Firm—Foley & Lardner

(57) ABSTRACT

An implantable infusion device includes of a disc-shaped housing that is made from a biocompatible material and contains a reservoir. The reservoir defines a chamber that contains at least one flexible diaphragm. A ring is provided in alignment with the peripheral edge of each diaphragm. The ring has a central opening that is aligned with the convolution and central portion of each diaphragm, to allow the diaphragm to flex within the ring. In this manner, the volume on one side of each diaphragm may be varied to correspond to a varying volume of infusion medium. Similarly, the volume within the reservoir chamber on the other side of the diaphragms is varied as the diaphragms flex, to correspond to the expansion and contraction of a propellant medium within the reservoir.

26 Claims, 6 Drawing Sheets

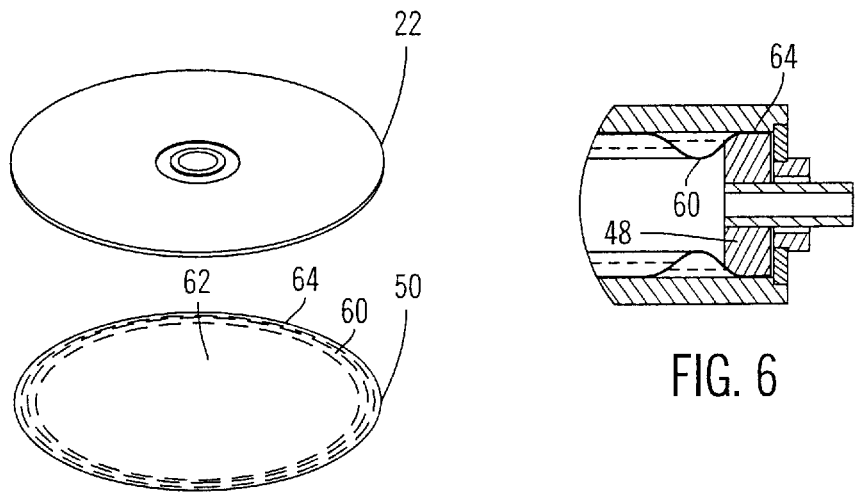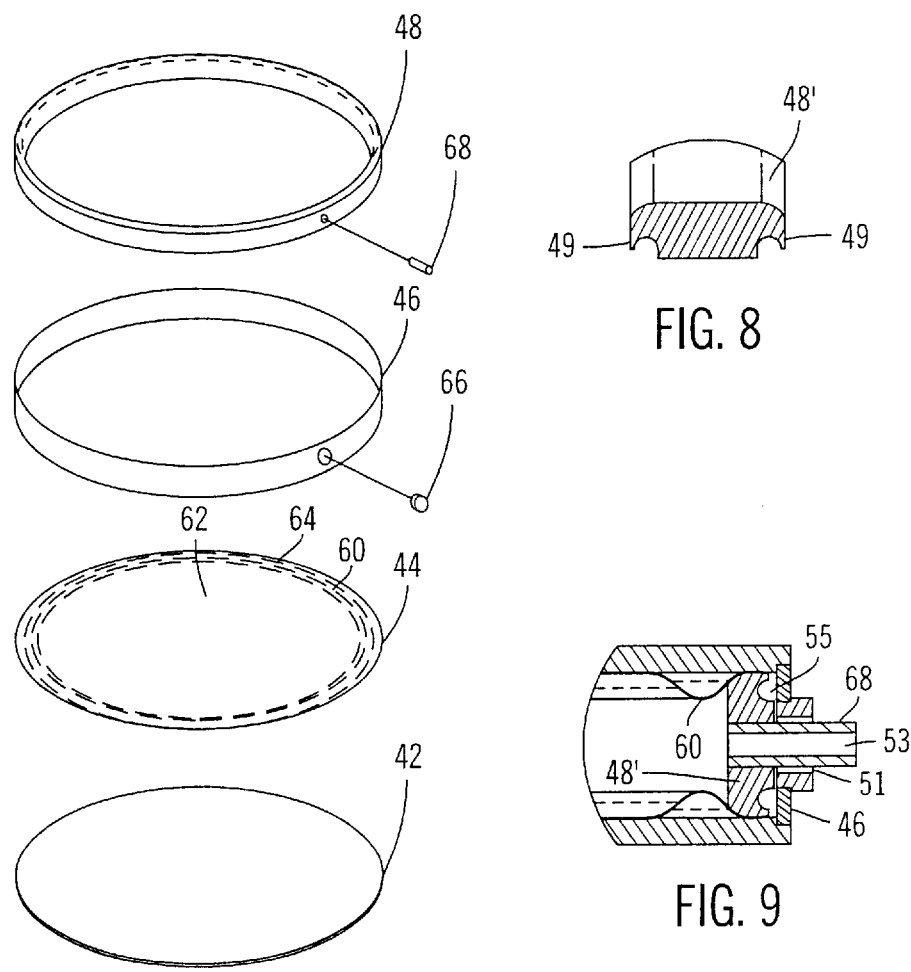
FIG. 7

IMPLANTABLE INFUSION DEVICE AND RESERVOIR FOR SAME

CROSS-REFERENCE TO RELATED APPLICATIONS

Embodiments of the present invention claim priority from a U.S. Provisional Application entitled "Implantable Infusion Device And Reservoir For Same," Serial No. 60/317,880, filed Sep. 7, 2001, the contents of which are incorporated by reference herein.

FIELD OF THE INVENTION

The present invention relates, generally, to implantable infusion devices having reservoirs and reservoir structures for such devices and, in preferred embodiments, to such devices and reservoirs configured to minimize the device thickness dimension, including methods of making and using the same.

RELATED ART

Implantable infusion devices are typically used to deliver an infusion media, such as a medication, to a patient. Such devices are typically designed to be implanted in a patient's body, to administer an infusion media to the patient at a regulated dosage.

Because implantable infusion devices are designed to be implanted in the patient's body, the dimensions of such devices can have an impact on the determination of the location on the body at which devices may be implanted, the level of comfort of the implant patient and the external appearance of the implant site. Typically, a device with relatively small dimensions and, in particular, a relatively small thickness dimension, will provide greater flexibility in the choice of location on the patient's body to place the implant and will minimize patient discomfort and minimize noticeable protrusions at the implant site. Accordingly, there is a need in the industry for implantable infusion device configurations with minimized overall dimensions and, in particular, with minimized thickness dimensions.

However, the volume of infusion media that a given device is capable of containing (also referred to as the volume capacity of the device) may be dependent, at least in part, on the dimensions of the device. Typically, smaller device designs have smaller volume capacities and, thus, require more frequent re-filling or replacement operations, as compared to larger devices. Thus, there is often a trade-off between benefits achievable with reductions in device dimensions (size reductions) and benefits of increasing or maintaining the volume capacity of the device. Accordingly, there is a further need in the industry for implantable infusion device configurations with improved volume capacities or which have minimized device dimensions with little or no reduction in volume capacity.

Typical implantable infusion devices include a generally disc-shaped housing having a diameter dimension and a thickness dimension. The thickness dimension of the device is dependent, at least in part, upon the relative placement of device components and the thickness dimensions of the device components. Such devices typically include a reservoir located within the housing for holding a volume of an infusion medium, for example, a liquid medication. Such devices also typically include an inlet for receiving infusion medium into the reservoir to fill or re-fill the reservoir, for example, from a hollow needle, such as a syringe needle.

In addition, implantable infusion devices may include a driving mechanism, such as a pump, for controlling the flow of infusion medium from the reservoir to the patient, through an outlet in the housing, either on a continuous basis, at scheduled or programmed times or in response to signals from a sensor or other signal source. Other devices include pressurized gas sources for driving infusion medium from the reservoir. Each of those components define a thickness dimension which, depending upon their placement on the device, may affect the overall thickness dimension of the implantable infusion device.

Example implantable infusion devices are described in U.S. Pat. No. 5,527,307, U.S. Pat. No. 5,514,103 and U.S. Pat. No. 5,176,644, each to Srisathapat et al. (and assigned to Minimed Technologies, Ltd.), U.S. Pat. No. 5,167,633 to Mann et al. (and assigned to Pacesetter Infusion, Ltd,), U.S. Pat. No. 4,697,622 to Swift (assigned to Parker Hannifin Corporation) and U.S. Pat. No. 4,573,994 to Fischell et al. (assigned to The Johns Hopkins University), each of which is incorporated herein by reference. Each of the above-cited patents describes an implantable infusion device which includes a generally disc-shaped housing containing a reservoir, a driving mechanism or pump, an inlet, an outlet and an electronic circuit for controlling the operation of the driving mechanism or pump.

With reference to the drawings in each of the above-cited patents, a significant portion of the thickness dimension of the illustrated implantable infusion devices is composed of the reservoir in those devices. For example, several of the above-cited patents describe reservoirs composed of a flexible bag within a medication chamber. One example is shown in FIGS. 7–10 of U.S. Pat. No. 5,176,644, where a flexible bag or sack 228 is formed of interconnected sheets of Halar film or the like. As illustrated, about one-half of the overall thickness dimensions of such devices is composed of the medication chamber and bag structure. The bag is filled with a pressure fluid that expands and contracts to inversely vary the volume of the portion of the medication chamber outside of the bag and to provide a relatively constant pressure on the medication in the medication chamber, as the medication is dispensed. However, in the pressurized bag arrangement, a repetitive compression and expansion of the flexible bag, as may occur after multiple fill and re-fill operations, can tend to wear and/or fatigue the bag and, possibly tear or otherwise impair the operation of the bag. In addition, plastics and Halar films can tend to allow infusion medium and/or propellant to diffuse through the bag material.

Other implantable infusion device configurations, such as shown in the '622 patent to Swift, employ a moveable diaphragm that cooperates with the lower shell of the device to define a pressurant chamber filled with gas pressurant and cooperates with an internal wall (base) to define a reservoir. The diaphragm shown in the Swift patent has multiple convolutions or waves which apparently are configured to match corresponding grooves and ridges formed in the lower shell and in the internal wall (or base). However, the groove and ridge configuration of the shell and internal wall tend to increase the thickness of the shell and internal wall, without providing a corresponding increase in volume capacity. In addition, multiple convolutions can increase the stiffness of the diaphragm and, thus, require a greater amount of energy to move the diaphragm. Furthermore, convolutions may provide additional stress or fatigue points on the diaphragm.

Yet other implantable infusion device configurations employ an expandable bellows structure secured within a chamber and filled with a pressurized gas. In such arrangements, one end of the bellows structure is secured to a wall of the chamber, while the other end is allowed to move toward and away from the opposite wall of the chamber, as gas outside of the bellows expands and contracts, as the bellows expands or contracts. The volume within the bellows defines a reservoir for the infusion medium. Because the bellows structure inherently includes multiple creases or joints, a significant portion of the volume of the reservoir tends to be unusable. In addition, such bellows structures tend to require relatively complex structures of welded plates and multiple welded joints, which can increase the cost and adversely affect the reliability of the infusion device. Furthermore, infusion media may tend to stagnate within the multiple creases or joints of the bellows structure, which may lead to aggregation, statification and chemical degradation.

Thus, there is a need for new and improved implantable infusion device configurations and reservoir configurations having reduced thickness dimensions and/or improved volume capacities, without compromising the operational life, reliability and efficiency of the device.

SUMMARY OF THE DISCLOSURE

The present invention relates generally to implantable infusion devices. Particular embodiments relate to reservoir structures for such devices and methods of making and using the same.

Embodiments of the present invention employ reservoir configurations that reduce the thickness requirements of the device for a given longitudinal dimension, while maintaining similar volume capacities as prior reservoirs. In addition, reservoir configurations according to embodiments of the invention allow multiple dispensing and fill or re-fill operations, with reduced risk of damage to the reservoir components. In this manner, an implantable device may be formed with a relatively thin housing, and yet provide the capacity for containing at least the same, or greater, volumes of infusion medium, as compared to prior reservoir configurations, without compromising the operational life span of the device.

An implantable infusion device according to an embodiment of the invention includes a generally disc-shaped housing that is made from a biocompatible material or is appropriately coated with a biocompatible material to obtain a desired biocompatibility. The housing contains a reservoir for holding a volume of infusion medium, such as, but not limited to, a medication to be administered to the patient.

The housing has an outlet through which the infusion medium may be expelled. The reservoir is coupled in fluid flow communication with the outlet. In some embodiments, a drive mechanism may be coupled in fluid flow communication with the reservoir, to drive infusion fluid out of the reservoir, through the outlet. In other embodiments, fluid may flow or be drawn from the reservoir by other suitable means.

The reservoir defines a chamber that contains at least one flexible diaphragm. Each diaphragm has an outer peripheral edge fixed within the chamber, a convolution adjacent the peripheral edge and a generally smooth central portion that is free to flex within the chamber, wherein the convolution enhances the flexibility of the diaphragm. A ring is provided in alignment with the peripheral edge of each diaphragm. The ring has a central opening that is aligned with the convolution and central portion of each diaphragm, to allow the diaphragm to flex within the ring. In this manner, the volume on one side of each diaphragm may be varied to correspond to a varying volume of infusion medium. Similarly, the volume within the reservoir chamber on the other side of the diaphragms is varied as the diaphragms flex, to correspond to the expansion and contraction of a propellant medium within the reservoir. In an alternative embodiment, the diaphragm edges may be free-floating within the chamber.

The above arrangements allow for a relatively thin configuration of a reservoir chamber containing one or more diaphragms, yet further allows for the storage of infusion medium within a significant portion of the reservoir chamber, with little or no unused space within the reservoir chamber. In addition, the configuration allows for multiple flexures of the diaphragm, with reduced risk of damage to the diaphragms.

BRIEF DESCRIPTION OF THE DRAWINGS

Referring now to the drawings in which like reference numbers represent corresponding parts throughout:

FIG. 6 is a cross-sectional view of a portion of the reservoir section shown at 6—6 in FIG. 5.

FIG. 7 is an exploded view of the reservoir section of FIGS. 3–5.

FIG. 8 is a cross-section view of an inner ring according to an embodiment of the invention.

FIG. 9 is a cross-sectional view of the same portion of the reservoir section shown in FIG. 6, but with the inner ring of FIG. 8.

DETAILED DESCRIPTION OF PREFERRED EMBODIMENTS

The following detailed description is of the best presently contemplated mode of implementing the invention. This description is not to be taken in a limiting sense, but is made merely for the purpose of illustrating the general principles of the invention. The scope of the invention is best defined by the appended claims.

As discussed above, the present invention relates generally to implantable infusion devices having reservoirs and reservoir structures for such devices. Preferred embodiments of the invention relate to such devices and reservoirs configured with a minimized thickness dimension, to minimize trauma to the implant recipient (referred to herein as the patient). The term "patient" is intended to refer to the entity in which the implantable devices are implanted, whether or not the implant is carried out for medical purposes. Accordingly, the term "patient" is not to be construed as a reference or limitation to a medical context.

Figure 1:
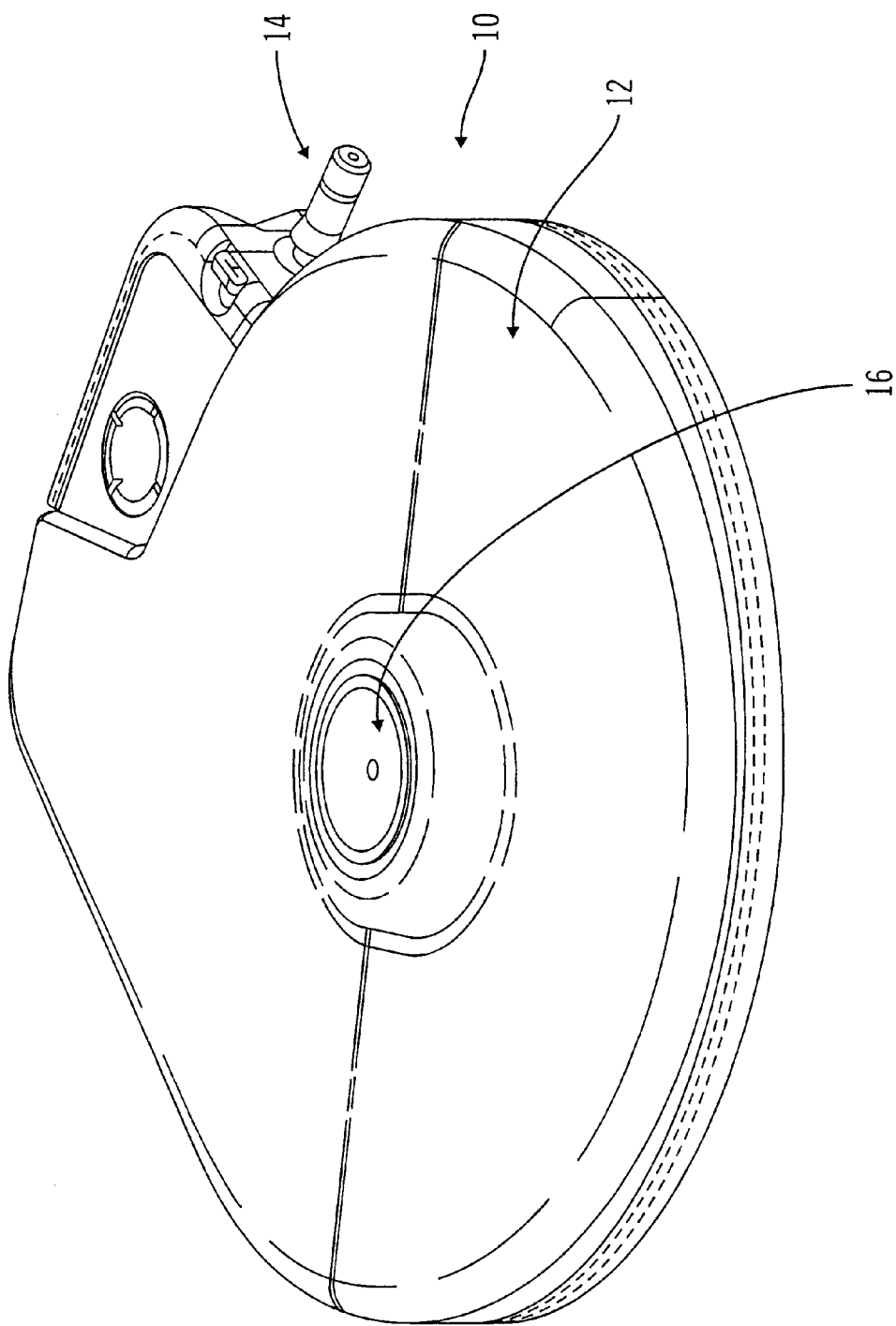
FIG. 1 is a perspective view of an implantable infusion device according to an embodiment of the invention.

FIG. 1 shows an implantable infusion device 10, according to an embodiment of the invention. The illustrated device 10 is configured to be surgically implanted into a patient. The device includes a generally disc-shaped housing 12 that is made from a biocompatible material or is appropriately covered with a biocompatible material to achieve a desired biocompatibility. The housing 12 contains a reservoir for holding a volume of infusion medium, such as, but not limited to, a drug or medication to be administered to the patient, a dye or other indicator to be administered into the patient, a cleaning fluid or the like.

The housing 12 has an outlet 14 through which the infusion medium may be expelled. When the device 10 is implanted in a patient, a catheter may be connected to the outlet 14, to deliver infusion medium expelled from the outlet 14 into the patient's blood stream or to a selected location in the patient's body. An inlet structure 16 is provided on the housing 12, for filling or re-filling the reservoir with infusion medium.

The disc-shaped housing configuration of the FIG. 1 has a diameter dimension D (shown in FIG. 2), defining the diameter of the disc, and a maximum thickness dimension T, defining the maximum thickness of the device. While FIG. 1 shows a circular disc-shaped embodiment, it will be understood that further embodiments of the invention may employ housings of other shapes, including, but not limited to, oval, oblong, rectangular, or other curved or polygonal shapes. In preferred embodiments, the housing 12 has no sharp corners, which may be accomplished by configuring the housing with no corners or with rounded corners and/or including rounded bumper portions around housing corners. Because the device is designed to be implanted in a patient's body, it is typically preferable to minimize the overall dimensions of the housing 12 and, in particular, the thickness dimension T, to minimize patient trauma during and after implantation surgery. It is also typically preferable to maximize the operational life of the device and to minimize the number of required re-fill, replacement or service operations.

Figure 2:
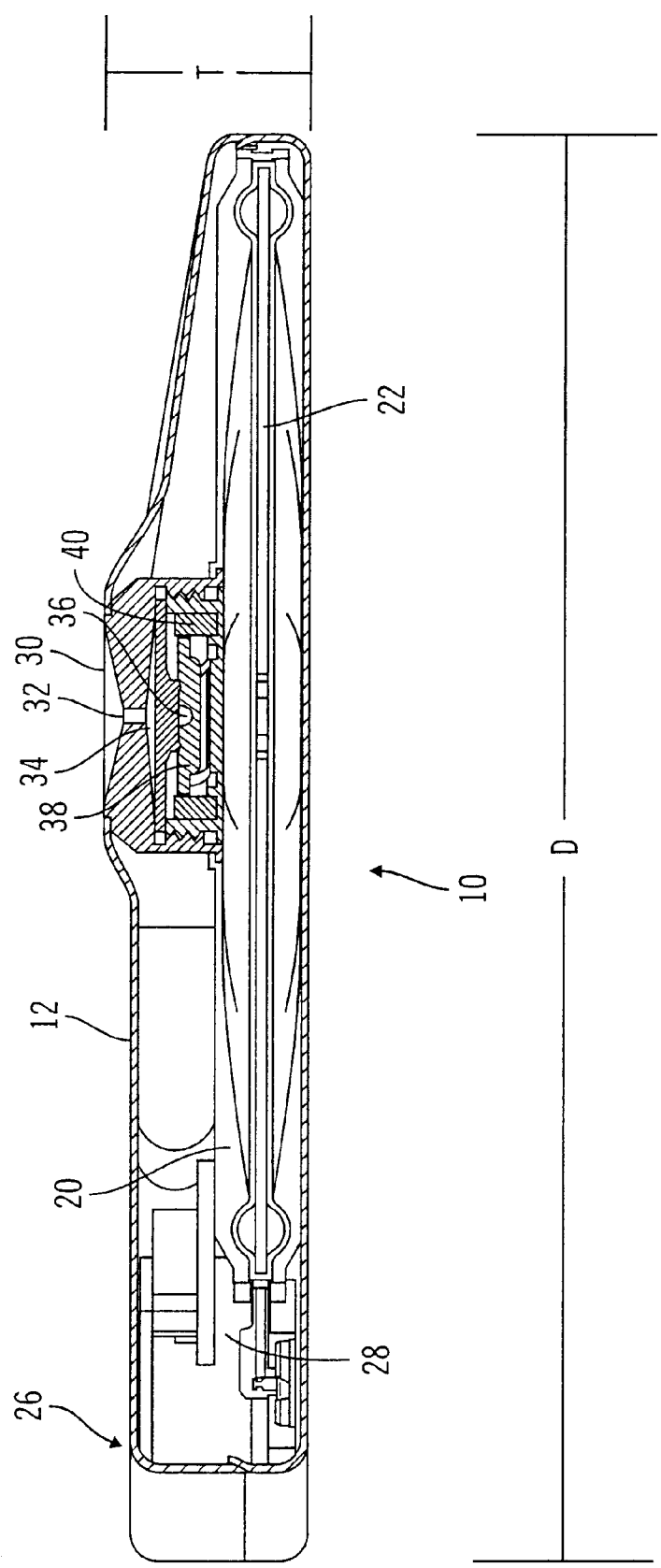
FIG. 2 is a cross-section view of the device of FIG. 1.

FIG. 2 shows a cross-sectional representation of the infusion device 10 of FIG. 1. As shown in FIG. 2, the housing 12 of the infusion device 10 includes a reservoir section 20, separated from other sections of the housing by a wall or cover 22. The housing 12 contains a reservoir in the reservoir section 20, for holding a volume of infusion medium, preferably at a controlled pressure. The housing 12 also contains a drive mechanism 26, such as a pump, and an electronic control system 28. In preferred embodiments, the drive mechanism 26 comprises a structure as described in co-pending U.S. Patent Application Serial No. 60/317,886, titled "Infusion Device and Driving Mechanism For Same," filed Sep. 7, 2001 under attorney docket no. 0204 (assigned to the assignee of the present invention), which is incorporated herein by reference. The electronic control system 28 includes a power source, such as a battery, and electronics for controlling the drive mechanism 26 to deliver infusion medium to the patient in a selected manner, for example, according to a programmed dispensing rate or schedule.

In the example embodiment of FIG. 2, the reservoir section 20 is located below the section of the housing containing the drive mechanism 26 and control electronics 28. In one embodiment, the portion of the housing 12 that contains the drive mechanism 26 and control electronics 28 is hermetically sealed from the external environment and from the reservoir section 20, while the portion of the housing 12 defining the reservoir section 20 need not be hermetically sealed. In such an embodiment, the section of the housing containing the drive mechanism 26 and control electronics 28 may be made from titanium or titanium alloy or other biocompatible metals (or may be made of other materials suitably coated with a biocompatible material), while the portion of the housing 12 defining the reservoir section 20 may be made from such metals or a biocompatible plastic.

The inlet structure 16 provides a closeable fluid flow path to the reservoir 24. The inlet structure 16 includes a conical-shaped receptacle 30 having an inlet opening 32 for receiving and guiding the tip of an hypodermic needle (not shown) through a septum 34 and into a fill chamber 36. One wall of the fill chamber 36 is defined by a moveable valve 38, which is arranged to be contacted and moved by a needle passing through the septum 34. When moved by a needle, the valve 38 opens a flow path 40 between the fill chamber 36 and the reservoir section 20. In preferred embodiments, the inlet structure 16 comprises a structure as described in co-pending U.S. Patent Application Serial No. 60/318,056, titled "Infusion Device and Inlet Structure For Same," filed Sep. 7, 2001 under attorney docket no. 0203 (assigned to the assignee of the present invention), which is incorporated herein by reference. However, other embodiments may employ other suitable inlet structures, including, but not limited to structures as described in U.S. Pat. No. 5,176,644, U.S. Pat. No. 5,514,103, and U.S. Pat. No. 5,527,307, each to Srisathapat et al., U.S. Pat. No. 5,167,633 to Mann et al, U.S. Pat. No. 4,697,622 to Swift and U.S. Pat. No. 4,573,994 to Fischell et al.

With reference to FIG. 2, the reservoir section of the housing 12 can account for a significant portion of the overall thickness dimension T of the device 10. Embodiments of the present invention employ reservoir configurations that reduce the thickness requirements of the device, as compared to prior reservoirs that have similar volume capacities. In addition, embodiments are configured to allow multiple dispensing and fill or re-fill operations, with reduced risk of damage to the reservoir components. In this manner, for a given longitudinal or diametric dimension, embodiments of the present invention may employ thinner housings, and yet provide the capacity for containing at least the same, or greater, volumes of infusion medium, without compromising the length of the operational life of the device, as compared to prior reservoir configurations.

The ability to reduce or minimize the device thickness dimension T, without compromising the reservoir volume capacity and operational life, can provide significant advantages with respect to patient comfort, appearance, flexibility in selecting implant locations on the body, and minimizing tissue erosion. In addition, smaller device dimensions may allow devices to be implanted in smaller patients, such as children. Accordingly, reservoir configurations that allow for reduced or minimized device thickness dimensions, as described herein, can provide significant advantages in the implantable infusion device technology.

Figure 3:
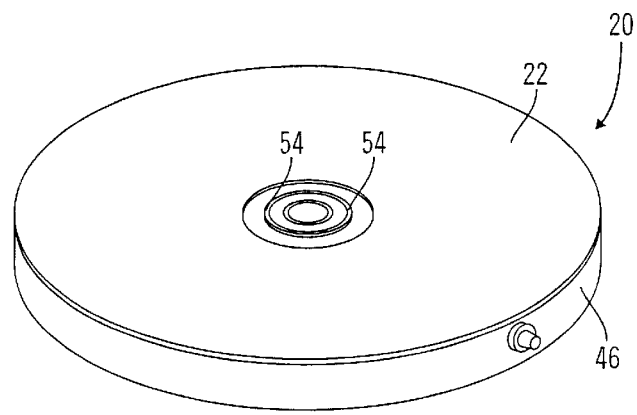
FIG. 3 is a perspective view of a reservoir section of an implantable infusion device according to an embodiment of the invention.
Figure 4:
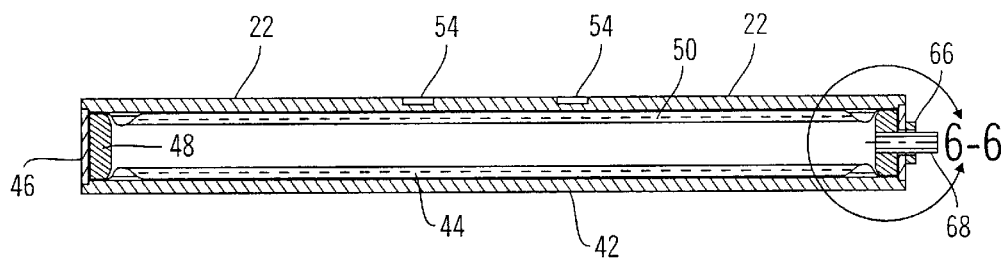
FIG. 4 is a cross-section view of a reservoir section of an implantable infusion device according to an embodiment of the invention, where the diaphragms are in a first state.
Figure 5:
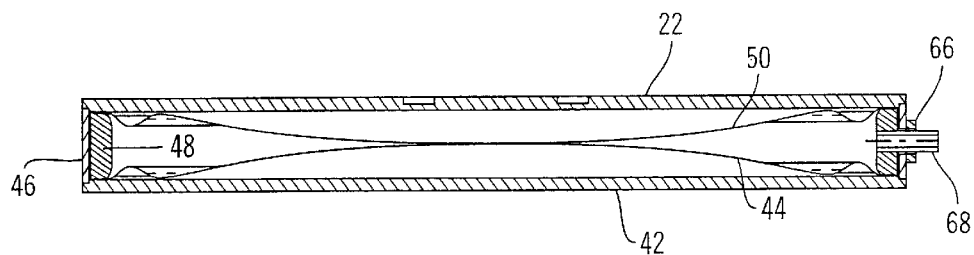
FIG. 5 is another cross-section view of the reservoir section of FIG. 3, where the diaphragms are in a second state.

A reservoir section configuration according to an embodiment of the present invention is illustrated in FIGS. 3–7, where FIG. 3 shows a perspective view of an assembled reservoir section 20, FIGS. 4 and 5 show cross-section views of the reservoir section with the reservoir diaphragms in two respective states, FIG. 7 shows an exploded view of the reservoir section and FIG. 6 shows a cross-section view of a component of the reservoir section.

The reservoir section 20 in FIGS. 3–7 includes a portion of the housing 12, comprising a bottom cover 42, a first flexible diaphragm 44, an outer ring 46 defining the outer wall of the reservoir section, an inner ring 48, a second flexible diaphragm 50, and a top cover 22. The top cover 22 corresponds to the same numbered item shown in FIG. 2. The top cover 22 is provided with one or more openings 54 that align with the flow path(s) 40 of the inlet structure, to provide a fluid flow path through the inlet structure and into the reservoir.

The top and bottom covers 22 and 42 and the outer ring 46, are preferably made from a suitably rigid material, including, but not limited to plastic, titanium, titanium alloy, stainless steel, cobalt alloy, or the like. Preferably, the outer ring material is infusion medium compatible or is coated with a suitable infusion medium compatible material. The inner ring 48 may also be made of the same or similar material. Each flexible diaphragms 44 and 50 is preferably made of a suitably flexible material, such as, but not limited to, a thin disc of titanium or titanium alloy, or the like. Preferably, the diaphragm material is infusion medium compatible or is suitably coated with an infusion medium compatible material.

In the illustrated embodiment, each flexible diaphragm 44 and 50 has an annular convolution or fold 60 adjacent, but slightly inward of its outer peripheral edge. As a result, each flexible diaphragm 44 and 50 comprises a central section 62, an annular convolution 60 surrounding the central section 62, and an outer peripheral lip 64 surrounding the annular crease or fold 60.

With reference to FIG. 7, a reservoir section 20 may be assembled by aligning and stacking a first diaphragm 44 and an outer ring 46 on a cover 42. An outlet fitting may be adhered to the outer ring and the outer ring 46 may be adhered to the cover 42 by, for example, but not limited to, a suitable adhesive, weld, brazing, solder, heat sealed plastic or the like. In preferred embodiments, the connection between the outlet fitting and the outer ring is a hermetic seal. The inner ring 48 is aligned on the outer peripheral lip 64 of the first diaphragm 44. A tube 68 may be adhered to and/or inserted through an aperture in the side of the inner ring 48. The second diaphragm 50 is then aligned on the stack, with the outer peripheral lip 64 of the second diaphragm 50 in contact with the inner ring 48. The cover 22 is then aligned onto the stack, in contact with the outer ring 46. The outer ring 46 may be adhered to the cover 22 in a manner similar to that described above with respect to cover 42. In an alternative embodiment, a subassembly of the inner ring 48 and diaphragms 44 and 50 is pre-assembled and, then, is inserted within the outer ring 46 and covered by covers 22 and 42. Upon assembly, the reservoir section 20 defines an interior space or chamber, in which the flexible diaphragms 44 and 50 may flex.

With reference to FIG. 6, when assembled, the lip 64 of the first diaphragm 44 is disposed between the inner ring 48 and the bottom cover 42. Similarly, the lip 64 of the second diaphragm 50 is disposed between the inner ring 48 and the top cover 52. The convolution 60 in each diaphragm 44 and 50 is disposed immediately to the inside of the inner ring 48. The lip 64 of each of the diaphragms 44 and 50 may be adhered to the inner ring 48 and/or the respective covers 42 and 52 by suitable adhesive, weld, or the like. Alternatively, the components may be held together by crimping the lip 64 between the ring and cover, in a tight-fitting arrangement, without the use of an adhesive material.

FIGS. 8 and 9 show a further embodiment of an inner ring 48' which functions similar to the inner ring 48 described above, but has a generally "T" shaped cross-section configuration. FIG. 8 shows a cross-section view of the "T" shaped configuration, while FIG. 9 shows the inner ring 48' within a reservoir section 20, similar to the view shown in FIG. 6. The "T" shaped configuration provides arms that can be formed with relatively thin sections 49 that engage the diaphragms 44 and 50. In this manner, the ring sections 49 may be formed to match (or at least be closer to) the thickness of the diaphragms, for an improved weld of the inner ring 48 with the diaphragms 44 and 50.

In the illustrated configurations, the flexible diaphragms 44 and 50 are held in place by effectively coupling the outer edge of each diaphragm to the inner ring 48. As a result, the central portion 62 of each diaphragm is free to flex, depending upon the pressure conditions within the chamber defined by the reservoir section 20. The diaphragms 44 and 50 have an inherent spring tension that provides a restoration force against flexure. By providing a volume of infusion medium on one side of each diaphragm and a propellant medium on the other side of each diaphragm, the pressure of the propellant gas cooperates with the natural restoration force of the diaphragms to, preferably, effect a controlled and/or constant pressure on the infusion medium, as the volume of infusion medium changes during dispensing or filling operations. In alternative embodiments, one or both diaphragms may be configured such that the natural state of the diaphragm imposes additional negative or positive force on the infusion medium and, preferably, imposes an amount of force dependent upon the percentage of the reservoir volume that is filled with infusion medium.

The annular convolution 60 can improve the ability of the diaphragms to provide a restoration force that is relatively constant over a larger amount of diaphragm flex, as compared to flat (convolution-less) diaphragms. In addition, the annular convolution 60 may help reduce tension on the diaphragm, which may improve the operational life of the diaphragm and reduce the risk of damage to a diaphragm that encounters multiple flexes during its operational life. More particularly, the annular convolution 60 in each diaphragm can increase the flexibility of the diaphragm, by, effectively, providing slack and, thus, reducing variances in tension that would otherwise occur as the diaphragm flexes between the first and second states. By reducing the tension and tension variances on the diaphragms, a more constant restoring force may be achieved and a greater number of fill and re-fill operations may be carried out on the reservoir section without damaging the diaphragms. In this manner, the annular convolution 60 can increase the operational life of each diaphragm and, thus, the reservoir.

Moreover, because the convolution 60 is disposed adjacent the outer periphery of each diaphragm, the convolution 60 does not take up a significant portion of the otherwise usable volume of the reservoir section 20 and the active area of the diaphragm is maximized. Furthermore, by locating the convolution in the peripheral region of the diaphragm (where diaphragm movement would otherwise be relatively small), the central portion of the diaphragm may be configured to move as a single, flat surface. While further embodiments may employ more than one annular convolution, a single annular convolution is preferred, as additional annular convolutions require a greater amount of force to move (or flex) the diaphragm.

In the illustrated embodiments, the diaphragms 44 and 50 have sufficient flexibility to move, preferably, between the first and second states shown in FIGS. 4 and 5. Preferably, the diaphragms provide a relatively constant restoring force throughout their flex between states. In FIG. 4, the diaphragms 44 and 50 are disposed in a first state, wherein the central portions 62 of the diaphragms are arranged generally flat against the inner surfaces of the bottom and top covers. In FIG. 5, the diaphragms are disposed in a second state, wherein the central portions 62 of the two diaphragms are flexed toward each other, relative to the first state.

The reservoir section 20 is preferably sealed against pressure. As noted above, the reservoir section 20 is configured to contain an infusion medium on one side of each diaphragm and a propellant medium on the opposite sides of the diaphragms. Thus, the reservoir section 20 includes a first volume for containing infusion medium and a second volume for containing propellant medium. The propellant medium is preferably a compressible material, such as Freon, flurocarbon, hydroflurocarbon, flurochlorocarbon, or the like, which expands and contracts to accommodate variances in the volume of infusion medium, as infusion medium is dispensed from or added (filled) into the reservoir and as the diaphragms flex to adjust for the change in infusion medium volume. In a preferred embodiment, the propellant medium provides a negative pressure on the diaphragms and expands or contracts to accommodate volumetric changes in the infusion medium. In other embodiments, the propellant medium provides a positive pressure on the diaphragms. In alternative embodiments, the restoring spring force of the diaphragms may provide sufficient pressure on the infusion medium, such that the propellant medium may be omitted.

In one embodiment, the reservoir section 20 may be configured to hold infusion medium in a first volume, comprising the volumes between the top cover 52 and the second diaphragm 50 and between the bottom cover 42 and the first diaphragm 44. A second volume, comprising the volume between the diaphragms 50 and 44, may hold the propellant. With reference to FIG. 9, in such an embodiment, the infusion medium outlet 51 of the reservoir may be arranged coaxial with a passage 53 that leads to the propellant medium volume between the diaphragms. More specifically, in the FIG. 9 embodiment, the outer ring 46 includes an outlet opening 51, communicating with the annular volume 55 in the reservoir. In addition, a tube 68 extends from the inner ring 48 and passes through the outlet opening 51. A small tube section or ring 66 may be disposed within an aperture in the ring 48 to define the opening 51. The tube 68 has an outer diameter which is smaller than the diameter of the outlet opening 51, such that a suitable clearance is provided within the opening 51, around the tube 68, to allow fluid flow from the annular volume 55 of the reservoir, through the clearance in the outlet opening. The tube 68 provides a flow passage to the volume between the diaphragms 44 and 50, within the reservoir.

Thus, in the FIG. 9 embodiment, the infusion medium volume between each diaphragm 50, 44 and its adjacent cover 52, 42 is in fluid flow communication with an annular volume 55 between the inner and outer rings 48 and 46, which is in fluid flow communication with the infusion medium outlet 51. Propellant medium may be added or removed from the propellant medium volume between the diaphragms 50 and 44, through the passage 53. Once a sufficient volume of propellant medium is input through the passage 53, the passage 53 may be plugged to inhibit escape of the propellant medium.

A drive mechanism, such as the pump shown at 26 in FIG. 2, may be coupled in flow communication with the volume of the reservoir between the diaphragm 50 and the cover 22, for driving infusion medium from the reservoir opening 51 and through the device outlet 14, as described above. Propellant may be added or removed from the volume between the diaphragms within the reservoir, through the tube 68. In such an arrangement, the second state of the diaphragms, as shown in FIG. 5, represents a filled state, while the first state of the diaphragms, as shown in FIG. 4, represents an empty state.

In operation, infusion medium may be added to the reservoir section 20, through the inlet structure 16 and openings 54, as described above. In addition, propellant medium may be added to the reservoir section 20, through tube 68. The diaphragms 44 and 50 will flex by an amount dependent upon the amount of the infusion medium and the pressure of the propellant medium within the reservoir and the spring tension of the diaphragms. The amount of propellant medium added to the reservoir section 20 may be selected and/or adjusted to provide a desired amount of pressure to cooperate with the minimum amount of the infusion medium and the spring tension of the diaphragms.

As infusion medium is added to the reservoir section, the medium causes the diaphragms to flex inward, toward each other, thus increasing the volume of the reservoir section between the diaphragm 50 and the cover 22 and between the diaphragm 44 and the cover 42. At the same time, the volume of the reservoir between the two diaphragms decreases, causing the propellant medium within that volume to compress.

As infusion medium is expelled from the reservoir either to deliver the infusion medium to the patient or simply to empty the reservoir, the volume of the reservoir section between the diaphragm 50 and the cover 22 and between the diaphragm 44 and the cover 42 decreases, while the volume between the two diaphragms increase. As the volume between the two diaphragms increases, the propellant medium within that volume expands (for example, more propellant transitions from liquid to gas phase). In this manner, the propellant medium can impart a continuous pressure on the diaphragms, and yet be capable of compressing and expanding to accommodate differences in volume of infusion medium.

In another embodiment, the reservoir section 20 may be configured to hold infusion medium within the volume defined between the two flexible diaphragms 44 and 50. In such an embodiment, the outlet 14 of the housing is provided in communication with the volume between the diaphragms. When the reservoir is filled, the diaphragms will separate and lay generally flat against the inner surfaces of the top and bottom covers, so as to take advantage of almost all of the available volume and minimize unused space within the reservoir section 20. As infusion medium is expelled from the reservoir section, the diaphragms 44 and 50 are allowed to flex toward each other, toward the state shown in FIG. 5.

In the embodiments described above with respect to FIGS. 4 and 5, each diaphragm may be provided with a single direction of motion from its rest position. The rest position of the diaphragm is the position when there is no pressure differential on opposite sides of the diaphragm that would otherwise cause the diaphragm to flex. Thus, in one embodiment, the rest positions of the diaphragms is shown in FIG. 4, wherein each diaphragm abuts against a respective cover 42 or 22 and is capable of flexing in only one direction from the rest position, away from the abutting cover. In another embodiment, the rest position of the diaphragms is shown in FIG. 5, wherein each diaphragm abuts against the other diaphragm. In that arrangement, each diaphragm is capable of flexing in only one direction from the rest position, away from the other diaphragm. In further embodiments, the rest position of one or both of the diaphragms 44 and 50 may be between the two states shown in FIGS. 4 and 5, such that the one or both diaphragms are capable of flex motion in two directions, toward and away from the other diaphragm.

In the above embodiments, the section of the reservoir that holds infusion medium may be pressurized with negative pressure relative to its operational environment. A negative pressure of up to about 14.7 p.s.i.a. and, more preferably, between about 0.5 and 10.0 p.s.i.a. In this manner, should a leak occur, fluid would most likely be drawn into the device from the outside environment, rather than fluid leaking out of the device into the environment. Where the operational environment is an implant site of a patient, it may be beneficial to avoid unwanted leakage of infusion medium into the implant site. In addition, negative pressure within the reservoir section 20 may assist in a fill or re-fill process, in that the negative pressure may, effectively, draw infusion medium out of a hypodermic needle, when the needle is inserted into the fill chamber 36 and the valve 38 is opened.

As discussed above, an infusion device according to embodiments of the invention may include a drive mechanism, such as a pump, for driving infusion medium out of the reservoir and through the device outlet. In further embodiments, the pressure provided by the propellant and/or the spring tension of the diaphragms may provide sufficient force to expel the infusion medium from the reservoir at the desired rate. Thus, by providing a propellant under suitable pressure, or by controlling the pressure of the propellant with a suitable pump mechanism connected in communication with the propellant volume, such as through the tube 68, the rate of expulsion of infusion medium from the device outlet may be controlled.

Figure 10:
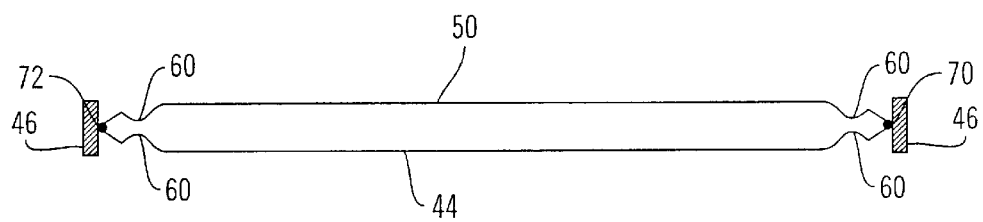
FIG. 10 is a cross-sectional view of a diaphragm arrangement according to an embodiment of the invention.

In the above embodiments, an inner ring 48 or 48' is disposed between the two diaphragms 44 and 50. In further embodiments, the peripheral edges or lips 64 of the two diaphragms may be jointed together and/or joined to the outer ring 46, for example as shown in FIG. 10. The joints 70 and 72 may be formed by adhering the lips 64 of the diaphragms together with a suitable adhesive, weld, mechanical crimp or combination. In one embodiment, the joints 70 and 72 are not fixed with respect to the outer ring 46 of the reservoir section. In other embodiments, the joints 70 and 72 are fixed relative to the outer ring 46 by, for example, adhering the joined diaphragm edges to the outer ring 46 by a suitable adhesive, weld, mechanical crimp or combination.

Figure 11:
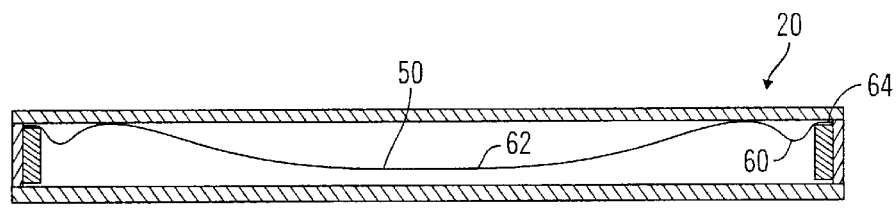
FIG. 11 is a cross-sectional view of a reservoir section according to a further embodiment of the invention.

In yet further embodiments, instead of employing two diaphragms, the reservoir section 20 includes a single diaphragm 50, as shown in FIG. 11. The diaphragm 50 includes an annular convolution 60, lip 64 and central section 62, as described above and, thus, makes available the advantages noted above. In the FIG. 11 embodiment, infusion medium may be disposed on one side of the diaphragm, while propellant may be disposed on the opposite side of the diaphragm. The operation of the device would otherwise be similar to that described above with respect to FIGS. 3–7.

Figure 12:
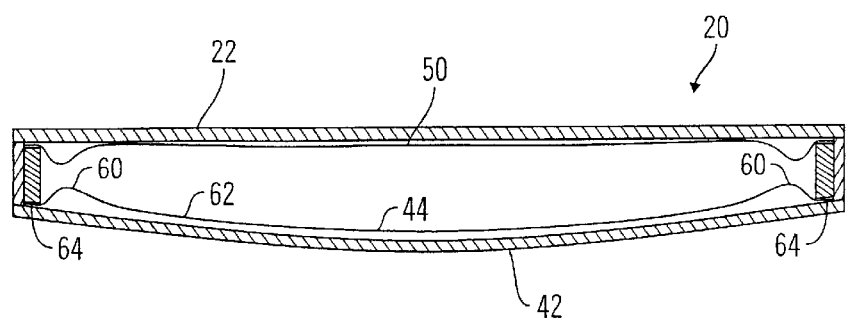
FIG. 12 is a cross-sectional view of a reservoir section according to yet a further embodiment of the invention.

In yet further embodiments, the bottom and/or top covers 42 and 52 are curved in a bowl-shape to match a curvature of the first and/or second diaphragms, when in a separated or first state, as shown in FIG. 12. In that embodiment, the curvature of one or both of the covers 42, 22 can provide additional usable volume within the reservoir section, without significantly increasing the overall width dimension W of the device.

In the above embodiments, the diaphragms are connected or fixed at their edges to the inner ring 48. In further embodiments, the inner ring may be omitted and the peripheral edges of the diaphragms may be connected together to form a free-floating propellant container within the reservoir. For example, in FIG. 13, a first diaphragm 50 is connected at its peripheral edge to the peripheral edge of a second diaphragm 44. As a result, the two diaphragms form an enclosed volume therebetween, for holding a propellant.

Figure 13:
FIG. 13 is a cross-sectional view of a pair of diaphragms for a reservoir according to a further embodiment of the present invention.
Figure 14:
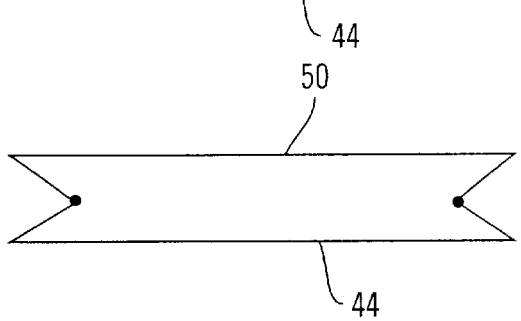
FIG. 14 is a cross-sectional view of a pair of diaphragms for a reservoir according to yet a further embodiment of the present invention.
Figure 15:
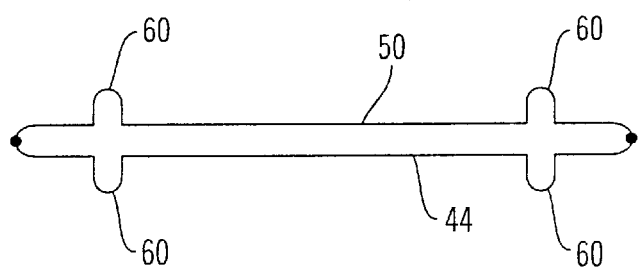
FIG. 15 is a cross-sectional view of a pair of diaphragms for a reservoir according to yet a further embodiment of the present invention.
Figure 16:
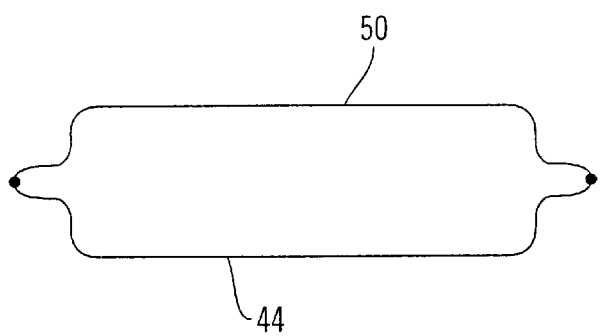
FIG. 16 is a cross-sectional view of a pair of diaphragms for a reservoir according to yet a further embodiment of the present invention.

In the FIG. 13, embodiment, the diaphragm 50 has a wavy configuration, while diaphragm 44 has a complementary wavy configuration. In other embodiments, the diaphragms may have a generally flat configuration or include one or more convolutions, such as a single convolution adjacent the peripheral edge, as discussed above with respect to other embodiments. In yet further embodiments, the diaphragms 50 and 44 may have a bellows-like shape, to provide a free-floating bellows configuration, when connected at their peripheral edges as shown in FIG. 14. Other floating or non-floating embodiments are shown in FIGS. 15 and 16.

Figure 17:
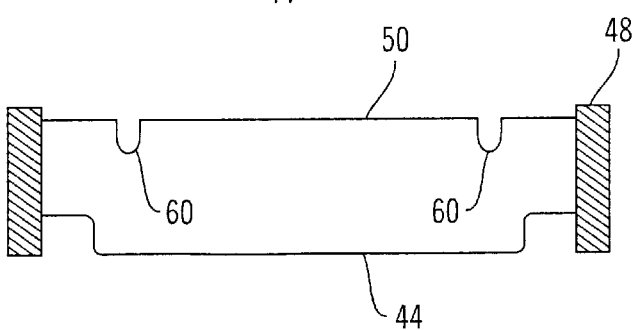
FIG. 17 is a cross-sectional view of a pair of diaphragms for a reservoir according to yet a further embodiment of the present invention.

A further embodiment is shown in FIG. 17, wherein each diaphragm 50 and 44 is connected, at its peripheral edge, to the inner ring 48. In the FIG. 17 embodiment, diaphragm 50 includes an annular convolution 60 and a generally flexible, flat central region surrounded by the annular convolution. The diaphragm 44 in FIG. 17 is distended to define a generally rigid or partially rigid, flat central region. The flexible central portion of the diaphragm 50 in FIG. 17 is designed to flex toward the central portion of diaphragm 44 and to take a shape that corresponds to the shape of the diaphragm 44, when in the flexed state.

Figure 18:
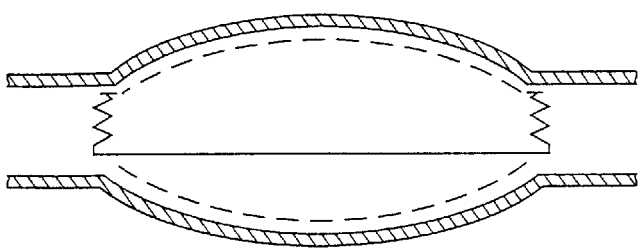
FIG. 18 is a cross-sectional view of a reservoir configuration according to yet a further embodiment of the present invention.

A reservoir configuration according to yet a further embodiment of the present invention is shown in FIG. 18, wherein the reservoir includes cover members 22 and 42 that are curved or bowed outward, to define concave surfaces in the interior of the reservoir. A single diaphragm 44 is disposed within the reservoir and is connected at its peripheral edge to the cover member 22. The diaphragm 44 in FIG. 18 has a bellows-like configuration, allowing it to expand and contract in a bellows-like fashion. The central portion of the diaphragm has is flexible or partially flexible, to conform to the shape of the concave inner surface of the cover member 42 or to the concave inner surface of the cover 22 (as shown in broken lines), depending upon the state of fill of the reservoir.

The foregoing description of the preferred embodiment of the invention has been presented for the purposes of illustration and description. It is not intended to be exhaustive or to limit the invention to the precise form disclosed. Many modifications and variations are possible in light of the above teaching. For example, while the above embodiments include inlet structures for filling or re-filling operations, other embodiments may not have an inlet structures, but instead are constructed as single use device designed to be implanted with a full reservoir and removed from the patient or not further used, once the reservoir is empty. Also, while embodiments described above employ drive mechanisms and/or propellants to drive infusion medium out of the reservoir, further embodiments of the infusion device may be configured to deliver infusion medium, without the requirement of a drive mechanism, control electronics or propellants. In such a configuration, the housing 12 need not include a portion containing a drive mechanism and control electronics.

What is claimed is:

1. An implantable infusion device for delivering infusion medium, the device comprising:
   a housing having a reservoir section and an outlet;
   a reservoir disposed within the reservoir section of the housing and coupled in fluid flow communication with the outlet, the reservoir defining a chamber that contains at least one flexible diaphragm, each diaphragm having an outer peripheral edge within the chamber, a convolution adjacent the peripheral edge and a generally flat central portion that is free to flex within the chamber, wherein the convolution enhances the flexibility of the diaphragm.

2. An implantable infusion device as recited in claim 1, wherein the at least one diaphragm comprises a pair of diaphragms.

3. An implantable infusion device as recited in claim 1, wherein the at least one diaphragm comprises first and second diaphragms and wherein the reservoir further contains a spacer disposed between the first and second diaphragms, to space the peripheral edge of the first diaphragm from the peripheral edge of the second diaphragm.

4. An implantable infusion device as recited in claim 3, wherein the spacer comprises a ring having a central opening to allow the central portions of the diaphragms to flex toward each other.

5. An implantable infusion device as recited in claim 1, wherein each diaphragm comprises a disc-shaped member having an annular peripheral edge and wherein the convolution of each diaphragm comprises an annular convolution disposed adjacent the annular peripheral edge of the diaphragm.

6. An implantable infusion device as recited in claim 1, wherein the reservoir further contains a ring disposed in alignment with the peripheral edge of each diaphragm, the ring having a central opening arranged in alignment with the convolution and the central portion of each diaphragm, to allow the central portion of each diaphragm to flex within the central opening of the ring.

7. An implantable infusion device as recited in claim 6, wherein the ring defines an inner peripheral edge and the convolution on each diaphragm is arranged immediately adjacent the inner peripheral edge of the ring.

8. An implantable infusion device as recited in claim 1, wherein the at least one diaphragm comprises a pair of diaphragms and wherein the reservoir further contains a ring disposed in alignment with the peripheral edge of each diaphragm, the ring having a central opening arranged in alignment with the convolution and the central portion of each diaphragm, to allow the central portion of each diaphragm to flex within the central opening of the ring toward the other diaphragm.

9. An implantable infusion device as recited in claim 8, wherein the ring defines an inner peripheral edge and the convolution on each diaphragm is arranged immediately adjacent the inner peripheral edge of the ring.

10. An implantable infusion device as recited in claim 1, wherein the reservoir section of the housing comprises an outer ring, a first cover disposed on one side of the outer ring and a second cover disposed on the opposite side of the outer ring to define an open interior between the first and second covers and within the outer ring, and wherein the reservoir chamber is provided within the open interior of the reservoir section.

11. An implantable infusion device as recited in claim 1, wherein:
   the at least one diaphragm comprises a pair of diaphragms;
   the reservoir further contains an inner ring disposed in alignment with the peripheral edge of each diaphragm, the inner ring having a central opening arranged in alignment with the convolution and the central portion of each diaphragm, to allow the central portion of each diaphragm to flex within the central opening of the inner ring toward the other diaphragm;
   the reservoir section of the housing comprises an outer ring, a first cover disposed on one side of the outer ring and a second cover disposed on the opposite side of the outer ring to define an open interior located between the first and second covers and within the outer ring, and
   the pair of diaphragms and the inner ring are provided within the open interior of the reservoir section.

12. An implantable infusion device as recited in claim 1, wherein the at least one diaphragm comprises a pair of diaphragms and wherein the peripheral edges of the pair of diaphragms are coupled together, while the convolution and central portion of each diaphragm is free to flex relative to the other diaphragm.

13. An implantable infusion device as recited in claim 1, wherein the at least one diaphragm comprises a pair of diaphragms defining a variable volume therebetween and wherein the outlet is coupled in fluid flow communication with the volume between the diaphragms.

14. An implantable infusion device as recited in claim 13, wherein a propellant medium is provided in the portion of the reservoir chamber that is not between the two diaphragms.

15. An implantable infusion device as recited in claim 13, further comprising a drive mechanism for driving fluid out of the volume between the diaphragms and through the outlet.

16. An implantable infusion device as recited in claim 13, further comprising an inlet for receiving infusion medium, the inlet provided in fluid flow communication with the volume between the diaphragms.

17. An implantable infusion device as recited in claim 1, wherein the at least one diaphragm comprises a pair of diaphragms defining a variable volume in the portion of the reservoir chamber that is not between the two diaphragms and wherein the outlet is coupled in fluid flow communication with the portion of the reservoir chamber that is not between the two diaphragms.

18. An implantable infusion device as recited in claim 17, wherein a propellant medium is provided in the portion of the reservoir chamber between the two diaphragms.

19. An implantable infusion device as recited in claim 17, further comprising a drive mechanism for driving fluid out of the portion of the reservoir chamber that is not between the two diaphragms and through the outlet.

20. An implantable infusion device as recited in claim 17, further comprising an inlet for receiving infusion medium, the inlet provided in fluid flow communication with the portion of the reservoir chamber that is not between the two diaphragms.

21. An implantable infusion device as recited in claim 1, wherein the reservoir section of the housing comprises a cover having a curved inner surface, and wherein the at least one diaphragm comprises a diaphragm having a curved central portion having a curvature that substantially matches the curvature of the curved inner surface of the cover.

22. A process of making an implantable infusion device, the process comprising:
providing a first diaphragm having a peripheral edge, a convolution adjacent the peripheral edge and a generally smooth central portion;
providing an inner ring having a central opening;
arranging the first diaphragm adjacent one side of the inner ring with the peripheral edge of the first diaphragm aligned with the inner ring and the convolution and central portion of the first diaphragm aligned with the central opening of the inner ring;
disposing the aligned first diaphragm and inner ring in a reservoir chamber; and
providing an outlet in fluid flow communication with one side of the first diaphragm.

23. A process as recited in claim 22, further comprising:
disposing an infusion medium on said one side of the first diaphragm; and
disposing a propellant medium on the opposite side of the first diaphragm.

24. A process as recited in claim 22, further comprising:
providing a second diaphragm having a peripheral edge, a convolution adjacent the peripheral edge and a generally smooth central portion;
arranging the second diaphragm adjacent the opposite side of the inner ring with the peripheral edge of the second diaphragm aligned with the inner ring and the convolution and central portion of the second diaphragm aligned with the central opening of the inner ring; and
disposing the aligned second diaphragm within the chamber,
wherein a first variable volume is defined between the first and second diaphragms and a second variable volume is defined as the portion of the reservoir chamber that is not between the first and second diaphragms.

25. A process as recited in claim 24, further comprising:
disposing an infusion medium in the first variable volume; and
disposing a propellant medium in the second variable volume.

26. A process as recited in claim 24, further comprising:
disposing a propellant medium in the first variable volume; and
disposing an infusion medium in the second variable volume.

* * * * *